(12) United States Patent
Sankaran

(10) Patent No.: US 8,177,812 B2
(45) Date of Patent: May 15, 2012

(54) BONE FUSION DEVICE AND METHODS

(75) Inventor: Meera Sankaran, Cupertino, CA (US)

(73) Assignee: Kyphon SARL, Neuchatel (CH)

( * ) Notice: Subject to any disclaimer, the term of this patent is extended or adjusted under 35 U.S.C. 154(b) by 0 days.

(21) Appl. No.: 12/807,337

(22) Filed: Sep. 2, 2010

(65) Prior Publication Data

US 2010/0331983 A1    Dec. 30, 2010

Related U.S. Application Data

(63) Continuation of application No. 11/967,780, filed on Dec. 31, 2007, now Pat. No. 7,799,056.

(51) Int. Cl.
*A61B 17/70* (2006.01)

(52) U.S. Cl. .................. 606/246; 606/254; 623/17.11; 623/17.16

(58) Field of Classification Search .......... 606/60, 606/103, 105, 246–264; 623/17.11–17.16
See application file for complete search history.

(56) References Cited

U.S. PATENT DOCUMENTS

| | | | |
|---|---|---|---|
| 4,422,451 A | 12/1983 | Kalamchi |
| 5,026,373 A | 6/1991 | Ray et al. |
| 5,059,193 A | 10/1991 | Kuslich |
| 5,702,395 A | 12/1997 | Hopf |
| 5,749,916 A | 5/1998 | Richelsoph |
| 5,976,187 A | 11/1999 | Richelsoph |
| 6,080,155 A | 6/2000 | Michelson |
| 6,102,950 A | 8/2000 | Vaccaro |
| 6,126,689 A | 10/2000 | Brett |
| 6,129,763 A | 10/2000 | Chauvin |
| 6,290,724 B1 | 9/2001 | Marino |
| 6,409,766 B1 | 6/2002 | Brett |
| 6,419,705 B1 | 7/2002 | Erickson |
| 6,436,140 B1 | 8/2002 | Liu et al. |
| 6,443,989 B1 | 9/2002 | Jackson |
| 6,491,695 B1 | 12/2002 | Roggenbuck |
| 6,582,467 B1 | 6/2003 | Teitelbaum et al. |

(Continued)

FOREIGN PATENT DOCUMENTS

EP    1552797    1/2000

(Continued)

OTHER PUBLICATIONS

International Searching Authority, International Search Report, Apr. 14, 2009.

(Continued)

*Primary Examiner* — Eduardo C Robert
*Assistant Examiner* — Christina Negrelli

(57) ABSTRACT

A bone fusion device, system, kit, and/or method can include an elongated structure including at least two anchor portions and at least one deformable segment connected on each end to one of the at least two anchor portions. Each deformable segment can include a plurality of spaced apart deformable members deformable from an unexpanded configuration to an expanded configuration. The bone fusion device may be implanted between two bone structures in the unexpanded configuration utilizing a minimally invasive surgical procedure. The deformable members can be compressed along a longitudinal axis of the device to deform the deformable members to the expanded configuration into contact with the two bone structures. A bone growth promoting material can be placed in the anchor portion lumen and in the interior of each deformable segment to promote bone in-growth between the bone structures.

24 Claims, 6 Drawing Sheets

U.S. PATENT DOCUMENTS

| | | |
|---|---|---|
| 6,652,533 B2 | 11/2003 | O'Neil |
| 6,695,760 B1 | 2/2004 | Winkler et al. |
| 6,749,613 B1 | 6/2004 | Conchy et al. |
| 6,764,515 B2 | 7/2004 | Ralph et al. |
| 6,773,460 B2 | 8/2004 | Jackson |
| 6,814,734 B2 | 11/2004 | Chappuis et al. |
| 6,821,298 B1 | 11/2004 | Jackson |
| 6,835,206 B2 | 12/2004 | Jackson |
| 6,893,464 B2 | 5/2005 | Kiester |
| 6,918,934 B2 | 7/2005 | Ralph et al. |
| 6,955,691 B2 | 10/2005 | Chae et al. |
| 7,011,658 B2 | 3/2006 | Young |
| 7,018,415 B1 | 3/2006 | McKay |
| 7,056,321 B2 | 6/2006 | Pagliuca et al. |
| 7,087,055 B2 | 8/2006 | Lim et al. |
| 7,118,598 B2 | 10/2006 | Michelson |
| 7,128,760 B2 | 10/2006 | Michelson |
| 7,141,070 B2 | 11/2006 | Ralph et al. |
| 7,153,281 B2 | 12/2006 | Holmes |
| 7,179,255 B2 | 2/2007 | Lettice et al. |
| 7,217,293 B2 | 5/2007 | Branch, Jr. |
| 7,226,451 B2 | 6/2007 | Shluzas et al. |
| 7,226,482 B2 | 6/2007 | Messerli et al. |
| 7,267,690 B2 | 9/2007 | Felt |
| 7,285,135 B2 | 10/2007 | McKay et al. |
| 7,291,152 B2 | 11/2007 | Abdou |
| 7,303,584 B2 | 12/2007 | Castro et al. |
| 7,799,056 B2 * | 9/2010 | Sankaran ...................... 606/246 |
| 2005/0143827 A1 * | 6/2005 | Globerman et al. ....... 623/17.16 |
| 2006/0212118 A1 | 9/2006 | Abernathie |
| 2007/0118171 A1 | 5/2007 | Reiley et al. |

FOREIGN PATENT DOCUMENTS

| | | |
|---|---|---|
| WO | WO 2005/004856 | 6/2005 |
| WO | WO 2006/134262 | 12/2006 |
| WO | WO 2007/009107 | 1/2007 |
| WO | WO 2007/022021 | 2/2007 |

OTHER PUBLICATIONS

International Searching Authority, Written Opinion, Apr. 14, 2009.

* cited by examiner

BONE FUSION DEVICE AND METHODS

CROSS REFERENCE TO RELATED APPLICATIONS

This application is a continuation of U.S. patent application Ser. No. 11/967,780 filed Dec. 31, 2007 now U.S. Pat. No. 7,79,056, the contents of which are hereby incorporated by reference in their entirety.

FIELD OF THE INVENTION

The present invention relates to bone fusion devices, systems, kits, and methods. Embodiments of the present invention can be used for fusion of joints, and may be particularly useful for fusion of intervertebral joints.

BACKGROUND

Spinal fusion, also known as spondylosyndesis, is a surgical procedure in which two or more vertebrae are fused together to stop the motion between them. Spinal fusion can be used to treat various pathological and/or traumatic conditions, including, for example: injury to the vertebrae; protrusion and/or degeneration of the intervertebral disc between vertebrae ("slipped" disc or herniated disc); abnormal curvatures of the spine (such as scoliosis or kyphosis); and a weak or unstable spine caused by infections or tumors. Spinal fusion can eliminate motion between vertebral segments, which can be a significant source of pain in some patients. The surgery can also stops the progress of spinal deformity, such as scoliosis.

Some approaches to spinal fusion include implanting a bone fusion device, or interbody cage, in the intervertebral space between adjacent vertebrae. Bone fusion devices can be used to distract adjacent vertebrae away from each other, or expand a collapsed disc space between two vertebrae. Restoring height to collapsed disc spaces can relieve painful pressure on nerves. Such devices can stabilize the vertebrae by preventing them from moving relative to each other while fusion occurs. Bone fusion devices can provide a space for inserting bone growth promotion material such as bone grafts and other bone growth promoting agents between adjacent vertebrae. Over time, the vertebrae and bone graft can grow together through and/or around the device so as to fuse the vertebrae.

Conventional bone fusion devices can have various configurations and may be implanted and/or operated in a variety of ways. For example, conventional bone fusion cages can be cylindrical, rectangular, elliptical, tapered, or other shapes. Such conventional devices may be hollow and can include openings through which bone growth promotion material can contact adjacent bone. Insertion of a bone fusion implant may be accomplished through an open surgical procedure through a relatively large incision. Alternatively, a bone fusion implant may be inserted using a minimally invasive surgical procedure, for example, through percutaneous insertion. Certain conventional bone fusion devices include external threads so that the device can be threaded into adjacent vertebrae having been drilled and tapped for that purpose.

Some conventional bone fusion devices comprise cylindrical cages having a width substantially equivalent to the height of the cage. Although larger heights may be clinically indicated, wider implants are generally not desirable since increased width requires removal of more bone for access to the intervertebral space, which can lead to decreased stability, and more retraction of nerve roots, which can lead to temporary or permanent nerve damage.

Other conventional bone fusion devices include vertebral support components (for example, plates) that are movable from a collapsed state to an expanded state. Such support plates may allow the width of the device to be varied so as to accommodate vertebrae of various sizes. These devices have disadvantages. For example, the support plates may require expansion prior to insertion, or the plates may be operatively connected by externally disposed linkage mechanisms, either of which can cause the device to have dimensions requiring an undesirably large incision for (minimally invasive) delivery to an intervertebral space. Other devices may be expandable after being inserted, but can be difficult to operate in a restricted space such as a collapsed intervertebral space.

Conventional bone fusion devices can involve other difficulties or be associated with other less desirable results. For example, some conventional fusion devices are designed to be impacted into the intervertebral space, which can lead to difficulty in placing the device in a desired position, and can unnecessarily traumatize the vertebral bodies or surrounding nerve and/or vascular tissue. Some of the interbody fusion devices rely on gravity alone to stabilize the device between vertebrae, which can lead to undesirable motion between the vertebrae and difficulty in achieving a complete fusion, at least without the aid of some additional stabilizing device, such as a rod or plate. Moreover, some of the devices are not structurally strong enough to support the heavy loads and bending forces at certain levels of the spine, in particular, the lumbar spine. The designs of some of bone fusion cages allow "stress-shielding" of the bone within the cage. Since bone growth is enhanced by stressing or loading the bone material, such "stress-shielding" can greatly increase the time for complete bone growth, or disturb the quality and density of the ultimately formed fusion mass.

Thus, what is desired is a bone fusion device that can be inserted in a minimally invasive manner, that is easily deployed, that provides strong and stable support between adjacent vertebrae, and that promotes optimal bone growth and spinal fusion.

SUMMARY OF THE INVENTION

Some embodiments of the present invention can include a bone fusion device having an elongated structure comprising at least two anchor portions and at least one deformable segment connected on each end to one of the at least two anchor portions. Each deformable segment can include a plurality of spaced apart deformable members deformable from an unexpanded configuration to an expanded configuration. The bone fusion device may be implanted between two bone structures in the unexpanded configuration, for example, utilizing a minimally invasive surgical procedure. The deformable members can be compressed along a longitudinal axis of the device to deform the deformable members to the expanded configuration into contact with the two bone structures.

In some embodiments, the expanded configuration of each deformable segment can comprise a predetermined configuration. In some embodiments, the device can further include at least two deformable segments. One of the deformable segments can be deformable to a first expanded configuration, and another one of the deformable segments can be deformable to a second expanded configuration different from the first expanded configuration.

In some embodiments, one end of the at least one deformable segment can be connected to a proximal anchor portion at a proximal end of the elongated structure, and another end of the at least one deformable segment can be connected to a distal anchor portion at a distal end of the elongated structure. An internal rod can extend through the elongated structure along the longitudinal axis and be detachably attached to the distal anchor. A pushing tube slidable about the internal rod and can be detachably attached to the proximal anchor portion. Translation of the pushing tube and the proximal anchor portion along the inner rod toward a fixed position of the distal anchor portion can compress the deformable members so as to deform each deformable segment to the expanded configuration.

In some embodiments, at least one of the anchor portions can have a hollow lumen and each deformable segment can have a hollow interior. A bone growth promoting material can be placed in the anchor portion lumen and in the interior of each deformable segment to promote bone in-growth between the bone structures.

The present invention can include embodiments of a bone fusion system and/or a bone fusion device kit. Such a system and/or kit can include embodiments of the bone fusion device, an internal rod detachably attachable to a distal anchor portion of the device, and an pushing tube detachably attachable to a proximal anchor portion of the device. Some embodiments of a system and/or kit can further include surgical instruments adapted for implanting the bone fusion device utilizing a minimally invasive surgical procedure. Some embodiments of a system and/or kit can further include a bone growth promoting material disposed in the bone fusion device.

Some embodiments of the present invention can include a method for fusing a bone comprising accessing an area between two bone structures utilizing a minimally invasive surgical procedure and delivering a bone fusion device between the two bone structures in an unexpanded configuration. The bone fusion device can comprise an elongated structure comprising at least two anchor portions and at least one deformable segment connected on each end to one of the at least two anchor portions, each deformable segment comprising a plurality of spaced apart deformable members deformable from the unexpanded configuration to an expanded configuration. The deformable members can be compressed along a longitudinal axis of the device so as to deform the deformable members to the expanded configuration into contact with the two bone structures. Certain embodiments of a method can further include providing a plurality of the bone fusion devices, each device having a different expanded configuration, and selecting one of the plurality of the bone fusion devices having a particular expanded configuration for use in a patient. In particular embodiments of a method, the at least one deformable segment can be deformed at least vertically along an intervertebral disc space height.

Features of a device, system, kit, and/or method of the present invention may be accomplished singularly, or in combination, in one or more of the embodiments of the present invention. As will be realized by those of skill in the art, many different embodiments of a device, system, kit, and/or method according to the present invention are possible. Additional uses, advantages, and features of the invention are set forth in the illustrative embodiments discussed in the detailed description herein and will become more apparent to those skilled in the art upon examination of the following.

DETAILED DESCRIPTION

Figure 1:
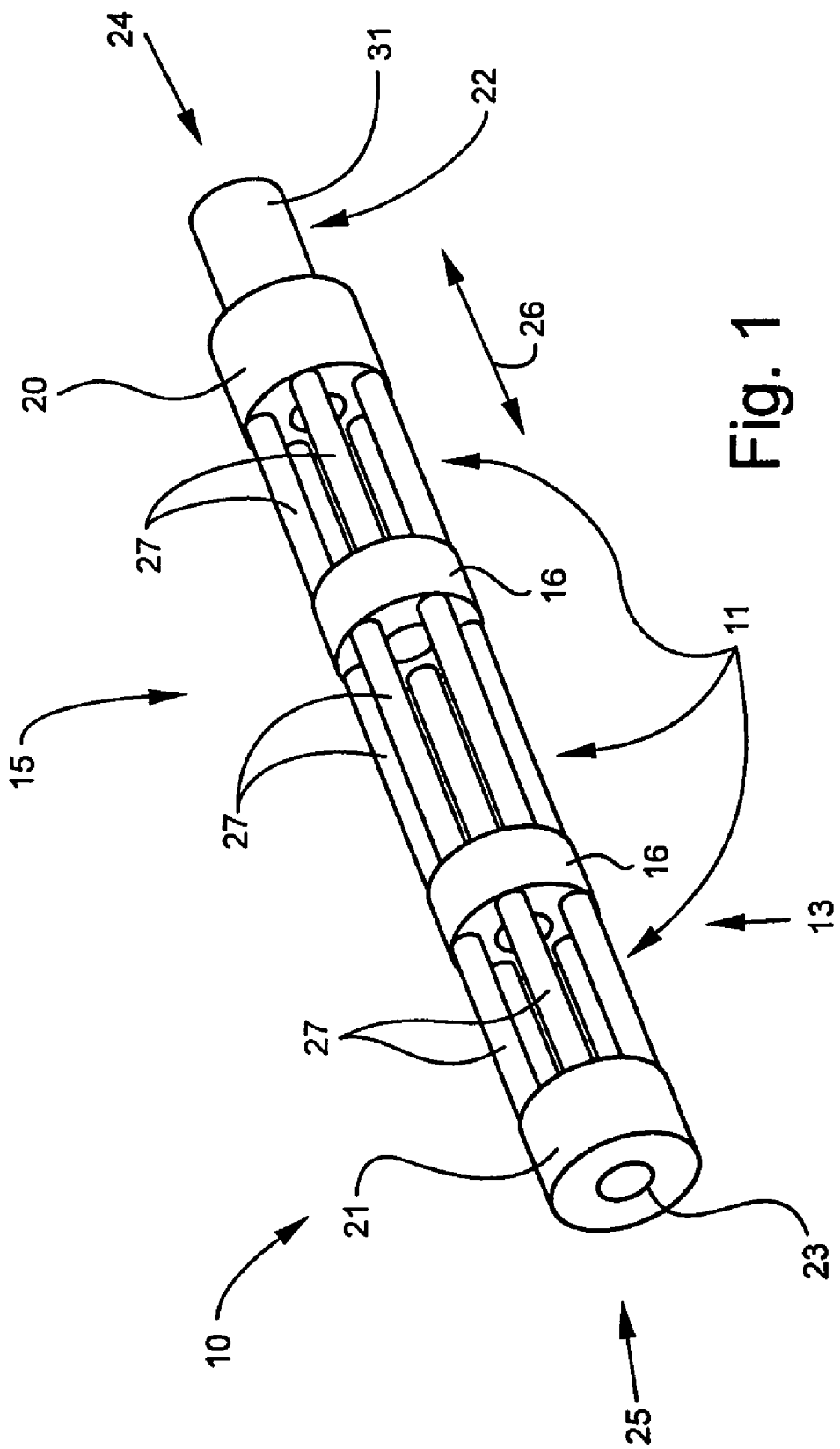
FIG. 1 is a perspective view of a bone fusion device having deformable segments alternating with anchor portions in an unexpanded configuration in an embodiment of the present invention.

For the purposes of this specification, unless otherwise indicated, all numbers expressing quantities, conditions, and so forth used in the specification are to be understood as being modified in all instances by the term "about." Accordingly, unless indicated to the contrary, the numerical parameters set forth in the following specification are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, for example, 1 to 6.1, and ending with a maximum value of 10 or less, for example, 5.5 to 10. Additionally, any reference referred to as being "incorporated herein" is to be understood as being incorporated in its entirety.

As used in this specification and the appended claims, the singular forms "a," "an," and "the" include plural referents unless the context clearly dictates otherwise. Thus, for example, the term "a projection" is intended to mean a single projection or a combination of projections. As used in this specification and the appended claims, "proximal" is defined as nearer to a point of reference such as an origin, a point of attachment, or the midline of the body. As used in this specification and the appended claims, "distal" is defined as farther from a point of reference, such as an origin; a point of attachment, or the midline of the body. Thus, the words "proximal" and "distal" refer to direction nearer to and farther from, respectively, an operator (for example, surgeon, physician, nurse, technician, etc.) who inserts a medical device into a patient, with the tip-end (i.e., distal end) of the device inserted inside the patient's body. For example, the end of a medical device inserted inside the patient's body is the distal end of the medical device, while the end of the medical device outside the patient's body is the proximal end of the medical device.

As used herein, a "desired" disc space, or "desired" disc space height, refers to the distance between two vertebrae which is determined to be appropriate for the particular condition of the patient. Thus, depending on the condition, the desired height may be that of the normal disc space when in a non-diseased condition, or the disc space may be greater than the normal disc space height or less than normal.

Some embodiments of the present invention include a bone fusion device 10 comprising deformable segments 11. Such a bone fusion device 10 having deformable segments 11 can be delivered to a target bone site, for example, an intervertebral space 12, in a compressed, or unexpanded, configuration 13. As a result, the bone fusion device 10 can provide the advantage of being capable of delivery to the intervertebral space 12 utilizing a minimally invasive surgical procedure. Once in a desired position within the intervertebral space 12, the deformable segments 11 can be expanded to a deployed, expanded configuration 14 in contact with the adjacent vertebral bodies 17. In certain embodiments, the deformable segments 11 may be expanded with a mechanical force. In certain embodiments, the deformable segments 11 may be deformed in varying degrees and configurations, which may allow for better control of the size and shape of the bone fusion implant 10 as compared to conventional bone fusion cages.

As shown in the illustrative embodiment in FIG. 1, the bone fusion device 10 can include an implantable elongated structure 15, for example, a cylinder or tube, of segments comprising at least two anchor portions 16 (for example, tubular anchor portions 16) and one or more deformable segments 11. The deformable segments 11 can be deformable into a deployed, expanded configuration 14 for contacting adjacent vertebral bodies 17. For purposes herein, "configuration" can mean the structural arrangement or form of the bone fusion device 10, deformable segments 11, and/or deformable members 27, including dimensions and degree and angle of expansion or collapse. Although described in terms of a "tube," the elongated structure 15 can have other geometric configurations, such as rectangular or oval, for example. Some embodiments can include a proximal anchor portion 20 and a distal anchor portion 21, as described herein with respect to FIGS. 1-4. In embodiments having a single deformable segment 11, the deformable segment 11 can be attached on one end to the proximal anchor portion 20 at a proximal anchor portion attachment point 22 near the proximal end 24 of the device 10, and on the opposite end to the distal anchor portion 21 at a distal anchor portion attachment point 23 near the distal end 25 of the device 10. In embodiments having more than one deformable segment 11, the deformable segments 11 can alternate with anchor portions 16. The alternating deformable segments 11 can be spaced at particular intervals along a longitudinal axis 26 of the device 11. The anchor portions 16 between the deformable segments 11 can have the same length such that the deformable segments 11 are spaced the same distance from each adjacent deformable segment 11. Alternatively, the anchor portions 16 can have different lengths such the deformable segments 11 are spaced at varying distances from other deformable segments 11. The spacing of the deformable segments 11 relative to the anchor portions 16 depends on factors including, for example, the elasticity modulus of the deformable segments 11 and the desired deployed configuration of the bone fusion device 10. Each deformable segment 11 can include a plurality of the spaced apart deformable members 27 deformable from the unexpanded configuration 13 to the expanded configuration 14. The deformable members 27 can be spaced apart about the perimeter, for example, the circumference, of the deformable segment 11 at various distances from adjacent deformable members 27. For example, each of the deformable members 27 can be spaced apart from adjacent deformable members 27 at equal distances between the deformable members 27.

Figure 3:
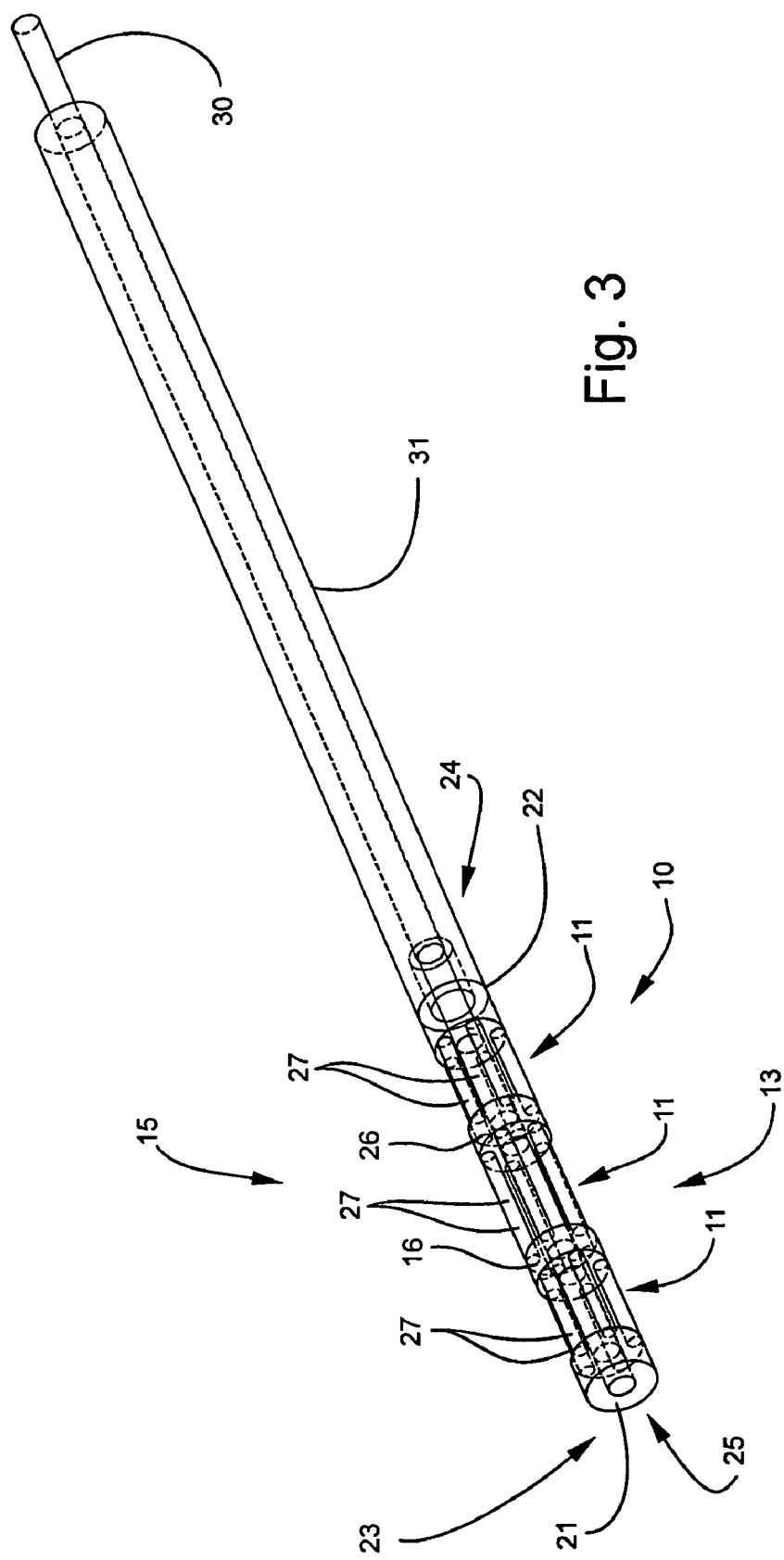
FIG. 3 is a perspective view of the bone fusion device in FIG. 1 in an unexpanded configuration, and an inner rod and a pushing tube attached to the bone fusion device, in an embodiment of the present invention.

As shown in the embodiments in FIGS. 1 and 3, the deformable segments 11 can comprise deformable members 27 lying parallel to the longitudinal axis 26 of the device 10. The deformable members 27 can be attached to the anchor portions 16 by an appropriate method, such as laserwelding. In certain embodiments, the deformable members 27 can be attached to the anchor portions 16 by other known methods. In other embodiments, the deformable segments 11 may be formed by cutting openings, such as with a laser, in tubular material extending between the anchor portions 16. In this way, the deformable segments 11 between the anchor portions 16 can be formed to have an open-mesh or open-grid configuration so as to permit the segments 11 to expand when compressed.

In some embodiments, the deformable members 27 can be spaced about the periphery, for example, the circumference, of the device 10 with equal spacing between the deformable members 27. In other embodiments, the deformable members 27 can be circumferentially spaced with varying sized spaces between the deformable members 27, depending on the desired deployed configuration of the deformable segment 11. Embodiments of the bone fusion device 10 can comprise various biocompatible materials, for example, titanium or stainless steel. The deformable members 27 can comprise such a material that is capable of being deformed into the expanded configuration 14 and maintaining that configuration for the duration of the functional life of the device 10. The functional life of the bone fusion device 10 may be a time sufficient for bone fusion to occur between adjacent bones or for permanent duration as a structural support. In certain embodiments, the anchor portions 16 can have a hollow interior, or lumen 28, so that bone growth promoting materials can be placed inside the anchor portions 16 and through the anchor portions 16 into and through the deformable segments 11.

Figure 4:
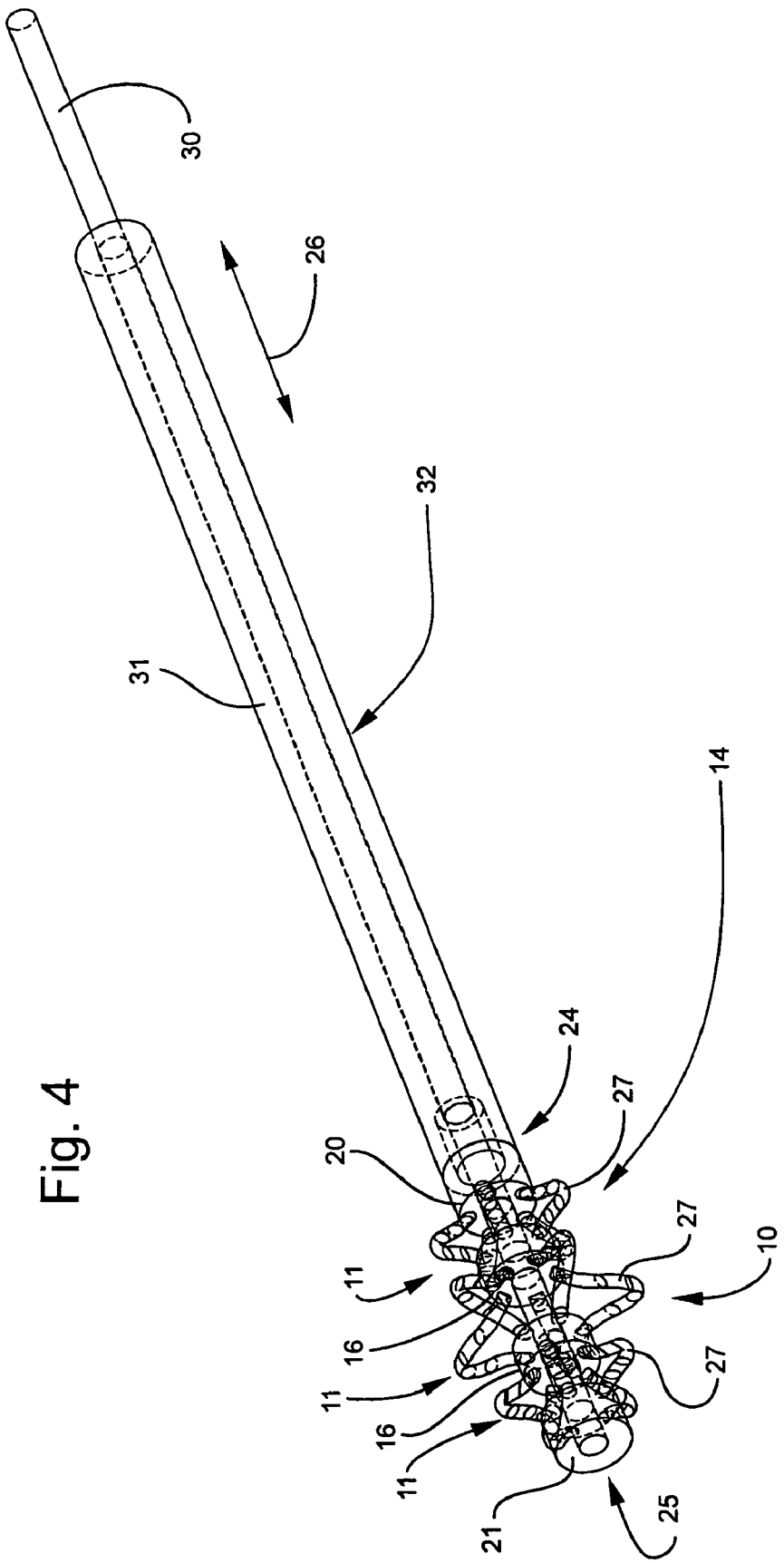
FIG. 4 is a perspective view of the bone fusion device and the inner rod and pushing tube attached to the bone fusion device in FIG. 3, the bone fusion device in an expanded configuration in an embodiment of the present invention.

Some embodiments of the bone infusion device 10 can further include an internal rod 30 and a pushing tube 31, as shown in FIGS. 3 and 4. The internal rod 30 and the pushing tube 31 can comprise a bone fusion device delivery and deployment system. In some embodiments, for example, as shown in FIGS. 3 and 4, the internal rod 30 can be detachably attached to the distal anchor portion 21 at the distal anchor portion attachment point 23, and the pushing tube 31 can be detachably attached to the proximal anchor portion 20 at the proximal anchor portion attachment point 22. The internal rod 30 may be attached to the distal anchor portion 21 with mating threads (not shown). For example, the distal tip of the internal rod 30 may have external threads that can be threaded into mating internal threads in the distal anchor portion 21. Likewise, the pushing tube 31 may be attached to the proximal anchor portion 20 with mating threads (not shown). For example, the distal tip of the pushing tube 31 may have internal threads that can be threaded onto mating external threads on the outer proximal surface of the proximal anchor portion 20. If both the internal rod 30 and the pushing tube 31 are detachably attached to the bone fusion device 10 using threads, the threads on each of the internal rod 30 and the pushing tube 31 can be identically sized as to allow for detachment of the internal rod 30 and the pushing tube 31 from the bone fusion device implant 10 by simultaneously rotating both the internal rod 30 and the pushing tube 31. In other embodiments, the internal rod 30 and/or the pushing tube 31 can be detachably attached to the bone fusion device 10 by other attachment mechanisms, such as with a locking pin or keyed structural fit between the internal rod 30 or pushing tube 31 and the fusion device 10.

In some embodiments, the internal rod 30 and the pushing tube 31 can operate together to cause the deformable members 27 to deform outwardly. The internal rod 30 and the distal end 25 of the bone fusion device 10 attached to the rod 30 can be held in a fixed or stationary position in the intervertebral space 12. The pushing tube 31 can be translated forward so as to push the proximal end 24 of the bone fusion device 10 attached thereto toward the fixed distal end 25 of the device 10. As the pushing tube 31 is translated forward, the linear compressive force of such translation/pushing along the longitudinal axis 26 of the device 10 can cause the deformable members 27 to deform outwardly, for example, radially. When the pushing tube 31 reaches its most forwardly translated (most distal) position 32, the deformable members 27 will have reached their fully expanded state, or configuration 14. In this configuration 14, all of the deformable members 27 can be bent at predetermined angles, depending on factors, including, for example, the arrangement of the deformable segments 11 relative to the anchor portions 16, and the gauge, shape, length, and number of deformable members 27. The bent deformable members 27 can serve to contact the adjacent vertebral body endplates 43 to restore the normal height, or a desired height, of the intervertebral disc 44 and to prevent movement of the implanted device 10 during its functional life.

Figure 5:
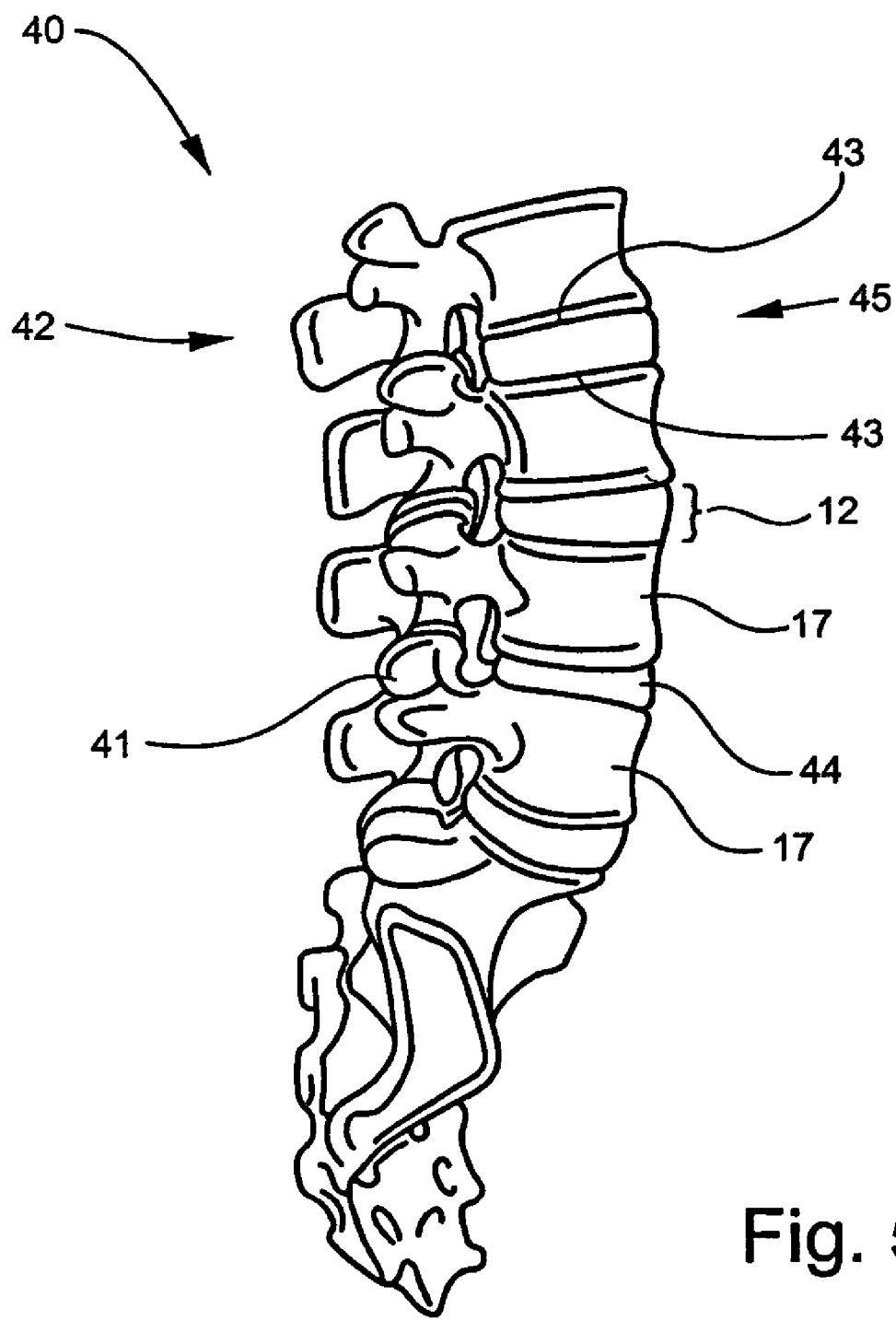
FIG. 5 is a side view of a portion of the anatomy of a spinal column in which some embodiments of the present invention may be useful.

Some embodiments of the bone fusion device 10 of the present invention can be inserted into the intervertebral space 12 in the unexpanded configuration 13, and then deployed into the expanded configuration 14 in situ. FIG. 5 is a side view of a portion of the anatomy of a spinal, or vertebral, column 40. The vertebral column 40 comprises a series of irregularly shaped bones, or vertebral bodies 17. The pedicle 41 is a projection that extends somewhat posteriorly 42 from the vertebral bodies 17. The upper and lower surfaces of each vertebral body 17 include an endplate 43. In between the vertebrae 17 interfacing with the vertebral endplates 43 are intervertebral discs 44 made of fibrous cartilage that act as shock absorbers and allow the back to move. The interveterbral discs 44 are oriented in the anterior 45 direction. As a person ages, these discs 44 can compress and shrink, resulting in a loss of height in the intervertebral disc space 12. Some embodiments of the bone fusion device 10 of the present invention may be useful for restoring the height of the intervertebral disc space 12 after the disc 44 has been removed due to degeneration, disease, or damage, and for promoting bone fusion between adjacent vertebral bodies 17.

Figure 6:
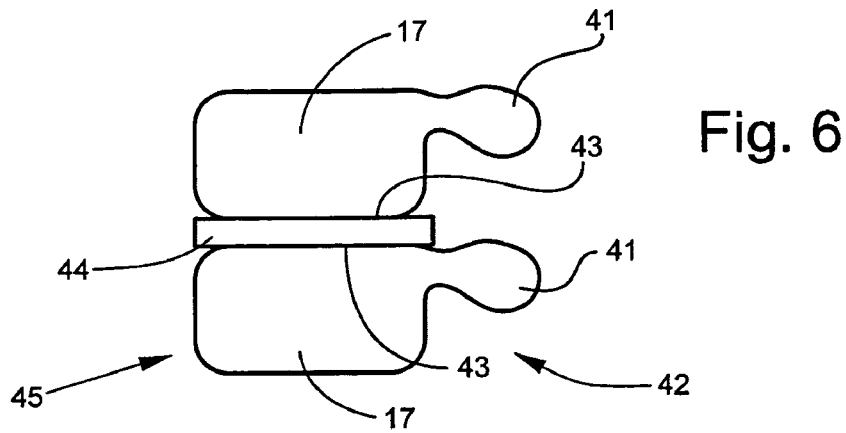
FIG. 6 is a diagrammatic side view of two vertebral bodies with an intervertebral disc in between the vertebral bodies.
Figure 7:
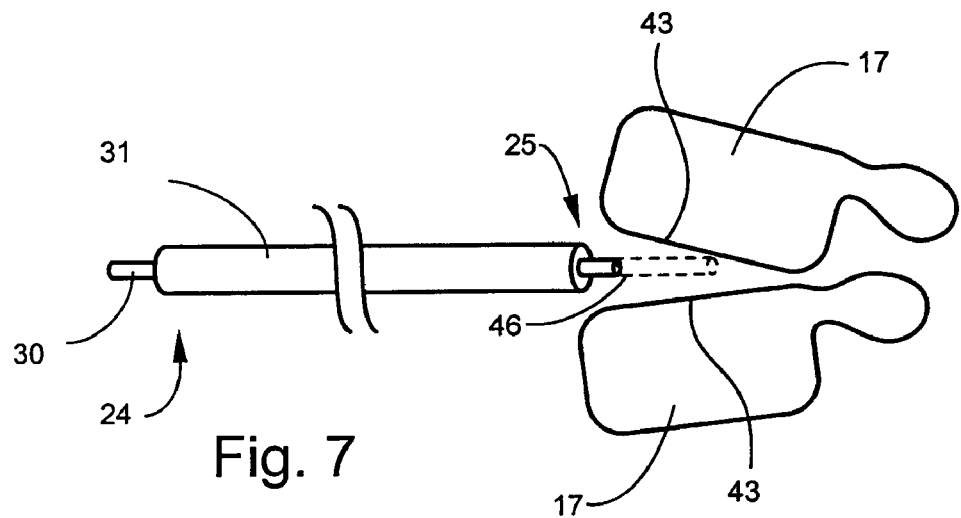
FIG. 7 is a diagrammatic side view of two vertebral bodies with the intervertebral disc removed and showing the inner rod and pushing tube in position to deliver the bone fusion device into the intervertebral space between the two vertebral bodies. The bone fusion device is not shown, but its position is represented in phantom lines.
Figure 8:
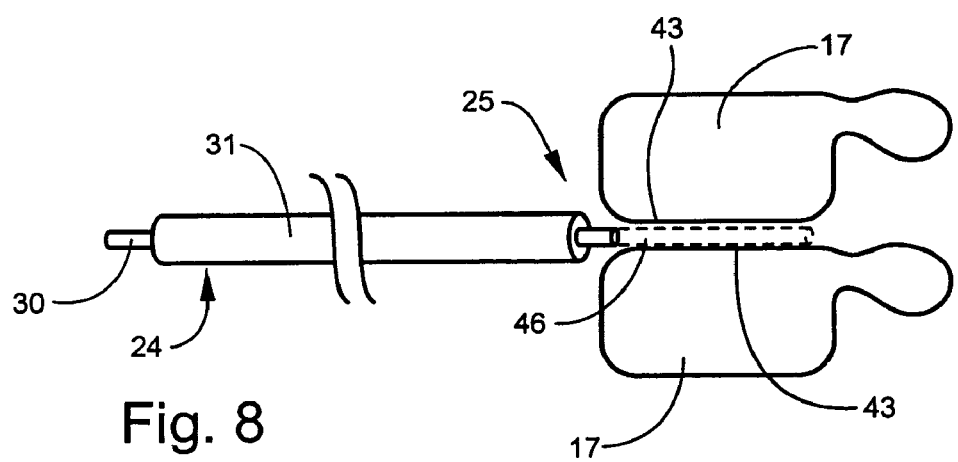
FIG. 8 is a diagrammatic side view of two vertebral bodies with the intervertebral disc removed and showing the inner rod and pushing tube in position after delivery of the bone fusion device into the intervertebral space between the two vertebral bodies. The bone fusion device is not shown, but its position is represented in phantom lines. The two vertebral bodies are separated to a desired intervertebral space height therebetween.

FIGS. 6-8 are diagrammatic side views of two vertebral bodies 17. FIG. 6 illustrates an intervertebral disc 44 in between the vertebral bodies 17. In FIGS. 7 and 8, the intervertebral disc 44 has been removed. FIG. 7 depicts the inner rod 30 and the pushing tube 31 in position to deliver the bone fusion device 10 into the intervertebral space 12 between the two vertebral bodies 17. In FIGS. 7 and 8, the bone fusion device 10 is not shown, but its position 46 is represented in phantom lines. FIG. 8 depicts the inner rod 30 and pushing tube 31 in position after delivery of the bone fusion device 10 into the intervertebral space 12 between the two vertebral bodies 17. The two vertebral bodies 17 are separated to a desired intervertebral space 12 height between the two vertebral bodies 17.

Various surgical approaches can be utilized to fuse vertebrae 17 using embodiments of the bone fusion device 10. The spine 40 may be approached and the bone fusion device 10 and bone growth promotion material (which may include a bone graft) placed either from the back (posterior 42 approach), from the front (anterior 45 approach), or a combination of both. For example, a posterior lumbar interbody fusion (PLIF) is performed from the back and includes removing the disc 44 between two vertebrae 17 and inserting the bone fusion device 10 and bone growth promoting material into the space 12 created between the two vertebral bodies 17. An anterior lumbar interbody fusion (ALIF) is similar to a PLIF, except that the disc space 12 is fused by approaching the spine 40 through the abdomen instead of through the back. A larger bone fusion device 10 and bone graft may be inserted from an anterior 45 approach. In a PLIF or ALIF procedure, the incisions can be large (for example, 3-6 inches). Alternatively, in an ALIF, the surgeon may use can a minilaparotomy technique with one small incision, or an endoscopic approach through several one-inch incisions. An anterior/posterior spinal fusion—from the front and the back—can be utilized for patients with a high degree of spinal instability (for example, fractures). Fusing both the front and back can provide a higher degree of stability for the spine 40 and a large surface area for the bone fusion, which can lead higher fusion rates. Another surgical approach for spinal fusion is the transforaminal lumbar interbody fusion (TLIF) performed from the side. The surgical approach selected for a particular spinal fusion can depend on a number of factors, including, for example, the section of the spine 40 involved, the type of disease, degeneration, or damage to be treated, and overall condition of the patient.

Embodiments of the bone fusion device 10 of the present invention can be inserted utilizing minimally invasive surgical techniques. Open surgical spinal fusion procedures can utilize a 4-6 inch incision. In contrast, minimally invasive spinal fusion can be performed with a small (for example, two centimeters) incision, or a percutaneous access portal, for access and delivery of instruments and the bone fusion device 10. Such minimally invasive surgery can utilize endoscopic equipment for viewing the surgical site. Due to the smaller access portal to the surgical site, miniaturized instruments, such as scrapers and drills, can be used to operate on the intervertebral space 12. In a minimally invasive procedure, the muscle can be split or moved apart rather than cut, as in an open procedure. As a result, minimally invasive spinal fusion procedures can provide decreased bleeding, less pain, a reduced hospital stay, shorter recuperating time, and less long term tissue damage.

Prior to implanting an embodiment of the bone fusion device 10 of the present invention, the target intervertebral site can be accessed, and at least a portion of the natural intervertebral disc 44 can be removed via a total or partial discectomy. The endplates 43 of the adjacent (upper and lower) vertebrae 17 can then be prepared using surgical instruments and techniques. For example, the endplates 43 of the bone can be scraped, curetted, chiseled, or a similar procedure performed to create an exposed vertebral body end surface 17 for facilitating bone growth across the fusion site. In some clinical circumstances, it may be advantageous to distract the adjacent vertebrae 17 prior to insertion of the bone fusion device 10. Such distraction can provide for easier removal of disc 44 material and/or greater exposure to facilitate preparation of the endplates 17. Distraction can also provide greater accuracy in determining the appropriate size bone fusion device 10 to implant. In some cases, an appropriately-shaped passage between and into the adjacent vertebrae 17 can be formed, for example, by drilling and/or tapping a bore of an approximate size for receiving the bone fusion implant 10. Following preparation of the intervertebral space 12, the bone fusion device 10 can be positioned within the space 12.

In a minimally invasive surgical procedure for inserting an embodiment of the bone fusion device 10, a surgeon may utilize a surgical access device (not shown) comprising an elongate delivery tube, or cannula. Such a surgical access device and minimally invasive technique is further described and shown in co-pending U.S. patent application Ser. No. 11/448,228, which is incorporated herein by reference in its entirety. The surgical access device may include a stylet for percutaneously inserting the delivery cannula to a surgical site. The stylet may include a handle for manipulating the stylet, a pointed tip, and a guide wire bore extending through the length of the stylet. The stylet can be inserted into a lumen of the elongate delivery cannula, and the guide wire bore of the stylet can be guided over a guide wire for positioning the delivery cannula at the surgical site.

The surgical access device may be percutaneously inserted to a targeted intervertebral 12 site using a variety of techniques. In one illustrative embodiment, a stab wound or small incision can be made in a patient's skin above a targeted surgical site. A small insertion cannula (not shown) having a sharp tip, for example, a trocar cannula, can be used to penetrate tissue to the surgical site. A guide wire (not shown) may be inserted through the insertion cannula. The insertion cannula can be removed, leaving the guide wire in place. With the stylet inserted in the lumen of the delivery cannula, the stylet and delivery cannula can then be threaded over the guide wire through the central guide wire bore in the stylet. The guide wire can have a diameter and rigidity sufficient to guide the delivery cannula accurately to the surgical site. When the delivery cannula is in a desired position, the guide wire and stylet can be removed from the delivery cannula. The bone fusion device 10 attached to the distal end 25 of the inner rod 30 can then be inserted through the lumen of the delivery tube to the intervertebral 12 site.

In another illustrative minimally invasive surgical procedure useful with embodiments of the present invention, the insertion cannula utilized to create an initial percutaneous route to the surgical site can be a Jamshidi needle (not shown). A delivery cannula can be threaded over the Jamshidi needle to the surgical site. When the delivery cannula is in a desired position, the Jamshidi needle can be removed from the delivery cannula. Alternatively, the insertion cannula and a guide wire, Jamshidi needle, or other insertion mechanism can be placed in the lumen of a stylet and/or delivery cannula and inserted together with the stylet and/or delivery cannula to the surgical site.

In certain embodiments, the proximal end 24 of the internal rod 30 and the pushing tube 31 can interface with an operating handle (for example, similar to the handle shown and described in co-pending U.S. application Ser. No. 11/731,707) positioned outside the patient's body. The internal rod 30 can interface with the handle so that the rod 30 and the distal end 25 of the bone fusion device 10 attached to the rod 30 can be held stationary. The pushing tube 31 can operatively interface with the handle so that the pushing rod 31 and the proximal end 24 of the bone fusion device 10 can be translated forward toward the stationary distal end 25 of the bone fusion device 10. For example, the pushing tube 31 may be operatively engaged with a translation wheel or a rack and pinion mechanism in the handle. The pushing tube 31 may thus be translated forward by rotating the translation wheel or moving the rack forward by rotating about the pinion gear.

The handle and the pushing tube interface can include a mechanism by which excessive translation of the pushing tube 31 and the proximal end 24 of the bone fusion device 10 can be prevented. For example, the handle may include indicia of the degree of deformable member expansion. Such indicia may indicate the distance the proximal end 24 of the bone fusion device 10 has compressed or another expression of the amount of expansion by the deformable members 27. Such indicia may correlate with the actual expanded dimension, for example, diameter or height, of the expanded deformable members 27.

Once the deformable segments 11 have been compressed along the longitudinal axis 26 of the bone fusion device 10 and thereby deformed into the expanded configuration 14, the inner rod 30 and the pushing tube 31 can be detached from the bone fusion device 10. If the inner rod 30 and the pushing tube 31 are both attached to the bone fusion device 10 at its distal and proximal ends, 25, 24, respectively, the inner rod 30 and the pushing tube 31 can be rotated simultaneously to detach from the bone fusion device 10.

In some embodiments, the deformable segments 11 can each have the same characteristics and dimensions. For example, each deformable segment 11 can comprise deformable members 27, for example, wire members, having the same wire material(s), have the same gauge, have the same shape (for example, round or rectangular), be the same length, and include the same number of wires 27 about the periphery, for example, the circumference, of the device 10. In certain embodiments, the deformable segments 11 can have different characteristics and dimensions relative to one or more other deformable segments 11. For example, the material(s) in the deformable wires 27 and the gauge, shape, length, and number of wires 27 in one segment 11 can be different than those characteristics in one or more other deformable segments 11. Varying the characteristics can allow a particular deformable segment 11 to deform more or less easily, to a greater or lesser degree, and/or more or less in one direction than in another segment 11. As a result, the ultimate diameter or configuration of each of the deformable segments 11 and of the overall device in its expanded configuration 14 can vary. This can allow the bone fusion device 10 to be customized for a particular joint, such as the intervertebral 12 joint, depending on factors such as the normal anatomy of that joint and the degree to which pathology or trauma can be repaired in a patient.

In some embodiments, the bone fusion device 10 can expand both along the height (or vertical transverse dimension) of the intervertebral disc space 12 and in a lateral direction (or horizontal transverse dimension) so as to provide a larger overall area for absorbing and/or distributing vertebral loads. Such multi-dimensional expansion of the deformable segments 11 can improve stability of the device 10 and/or resistance to subsidence of the device 10 into the adjacent vertebral bodies 17. In some embodiments, longitudinal compression of the proximal anchor portion 20 toward the distal anchor portion 21 of the bone fusion device 10 can provide uniform expansion of the deformable members 11 along the longitudinal axis 26 of the device 10. In other embodiments, the rate of expansion along the transverse axes need not necessarily be equal. Instead, some of the deformable members 27 oriented in a particular direction in one or more deformable segments 11 may be configured to provide a different rate and/or degree of expansion in that direction. As a result, the unevenly expanded deformable members 27 can provide customizable deployed configurations of the device 10 adapted to interface with and support particular anatomical configurations.

Figure 2:
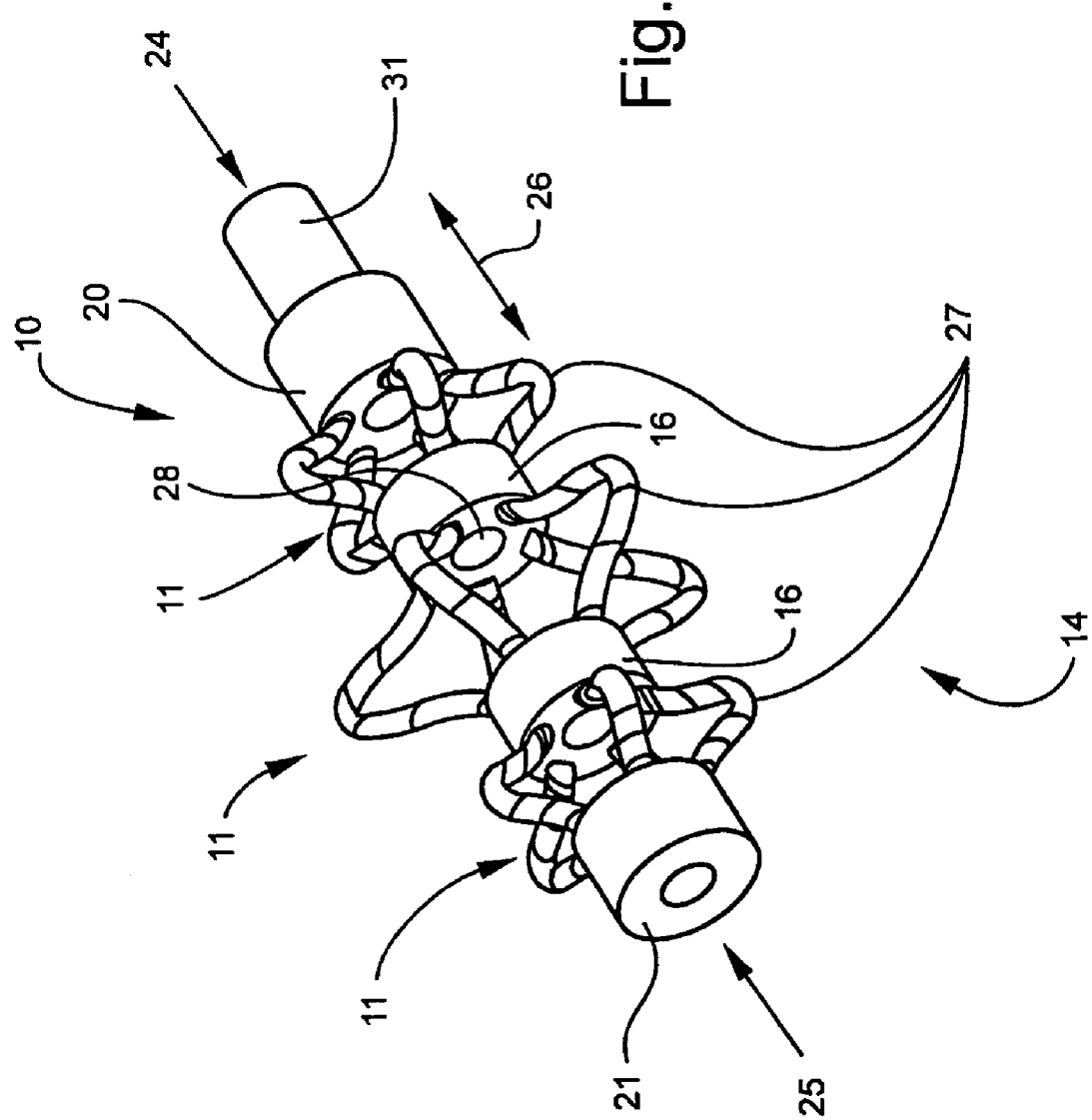
FIG. 2 is a perspective view of the bone fusion device in FIG. 1, showing deformable members of the deformable segments in an expanded configuration in an embodiment of the present invention.

As shown in the example of the embodiment in FIG. 2, the bone fusion device 10 can include the proximal anchor portion 20 and the distal anchor portion 21. Three deformable segments 11 alternating with two anchor portions 16 can be disposed between the proximal and distal anchor portions 20, 21, respectively, along the longitudinal axis 26 of the device 10. The deformable members 27 in the deformable segments 11 adjacent the proximal and distal anchor portions 20, 21, respectively, can be the same length. The deformable members 27 in the middle deformable segment 11 can be longer than the deformable members 27 in the deformable segments 11 adjacent the proximal and distal anchor portions 20, 21, respectively. As a result of this difference in length of the deformable members 27, when the bone fusion device 10 is compressed longitudinally, the deformable members 27 in the middle deformable segment 11 can deform to a larger dimension (for example, diameter) than the deformable members 27 in the deformable segments 11 adjacent the proximal and distal anchor portions 20, 21, respectively. Accordingly, by varying the characteristics, such as length, of the deformable members 27 in various deformable segments 11, the bone fusion device 10 can be designed to provide customized configurations when deployed in its expanded state 14.

As another example, the bone fusion device 10 may be utilized in an intervertebral space 12 in which there is normally a lordotic (anterior) curve, such as in the lumbar spine, or in an intervertebral space 12 in which there is normally a kyphotic (posterior) curve, such as in the thoracic spine. When diseased or damaged natural disc material is removed, the normal lordotic or kyphotic curvature of the spine 40 can be disadvantageously reduced or eliminated. Some embodiments of the present invention can help maintain and/or restore the natural anatomy of a fused spinal 40 segment. For example, a segment 11 of deformable members 27 on one end of the bone fusion device 10 can be configured to deform to a greater degree than one or more segments 11 of deformable members 27 in the remainder of the device 10. The end of the device 10 having the segment 11 of deformable members 27 capable of deforming to a greater degree can be inserted into the intervertebral space 12 so as to match the portion of the space 12 (either anterior 45 or posterior 42) having a normally greater distance between the vertebral bodies 17. In a similar manner, the end of the bone fusion device 10 configured to deform, or expand, to a greater degree can be used to push against a more severely collapsed portion of the vertebra 17.

In some embodiments, the deformable members 27 can have strength sufficient to maintain the device 10 in its expanded geometry 14 when exposed to compressive forces translated through the adjacent vertebral bodies 17.

In certain embodiments, the deformable members 27 can be pre-stressed so that when deformed from their small, unexpanded delivery configuration 13, the deformable members 27 will bend into particular directions. For example, the deformable members 27 may be pre-stressed on the portion of the deformable segment 11 circumference that will be oriented upwardly and downwardly toward the vertebral body endplates 43. In such an embodiment, when the bone fusion device 10 is in position in the proper orientation in the intervertebral space 12, the deformable members 27 can be deformed so that they deploy in a vertical direction into contact with the vertebral body endplates 43 above and below the device 10 but not in a lateral, or horizontal direction.

In some embodiments, the characteristics and dimensions of the deformable segments 11 can be varied to provide a configuration or other features that promote anchoring of the expanded deformable segments 11 into adjacent vertebral body endplates 43. For example, the deformable members 11 may be bent to interface with a particular contour of the endplate 43 (either natural or prepared). In certain embodiments, the surface of the deformable members 27 can comprise other structural features by which the expanded deformable segments 11 can securely engage the adjacent vertebral body endplates 43. For example, the deformable members 27 can have a textured or roughened surface and/or projections extending outwardly from the deformable members 27 for frictionally engaging and/or embedding into the vertebral endplates 43.

In certain embodiments, the bone fusion device 10 can include portions that are radiopaque such that delivery and deployment procedures can be visualized under fluoroscopy. In other embodiments, the bone fusion device 10 can be completely radiolucent so that the forming fusion mass in and about the bone fusion device 10 can be visualized radiographically without interference from the device 10.

In certain applications, one of the bone fusion devices 10 may be delivered into a first side of the target intervertebral space 12 and another one of the bone fusion devices 10 may be delivered into a second side of the target intervertebral space 12. That is, certain embodiments of the bone infusion device 10 can have a deployed size and configuration such that more than one of the devices 10, for example, two of the devices 10, can be deployed in the intervertebral space 12. In particular embodiments, a first and a second bone fusion device 10 can be positioned in the intervertebral space 12 in adjacent side-by-side relation. Such design variability can provide a surgeon with options for implanting the bone fusion device(s) 10 suited for particular patients.

In some embodiments of the bone fusion device 10, bone growth promoting materials can be loaded or inserted into the interior of the device 10 to facilitate or promote bone growth with and between the adjacent vertebral bodies 17. In some embodiments, the bone growth promoting material can comprise, for example, a bone graft material, such as bone chips or bone marrow, a bone morphogenic protein (BMP), a demineralized bone matrix (DBM), mesenchymal stem cells, a LIM mineralization protein (LMP), and/or any other suitable bone growth promoting material or substance. The bone graft material can be heterologous (xenograft), homologous (allograft), or autologous (autograft) bone, and/or derivatives thereof.

The bone growth promoting material can be loaded into the bone fusion device 10 prior to implantation of the device 10 in the intervertebral space 12. Alternatively, or in addition, the bone growth promoting material can be injected (or packed or loaded) into the bone fusion device 10 after the device 10 is implanted. The bone growth promoting material can be injected into the bone fusion device 10 before or after the deformable segments 11 are expanded into the deployed configuration 14. When the deformable segments 11 are expanded, individual deformable members 27 can separate from each other to create a predominantly open structure, as shown in FIGS. 2 and 4. The volume occupied by the expanded deformable member structure, or cage, is less than that of conventional bone fusion cages. Such an open structure can minimize restriction of movement of the bone growth promoting material and thus facilitate contact of the bone growth promoting material in the device 10 with adjacent vertebral bodies 17. As a result, the expanded configuration 14 of the bone fusion device 10 of the present invention can promote increased bone growth about and through the device 10.

Such embodiments of the bone fusion device 10 having deformable segments 11 have several advantages over conventional bone fusion devices 10. Some advantages include, for example, being insertable in the unexpanded, or collapsed, configuration 13 into a space between bones using a minimally invasive surgical procedure; being expandable to a deployed configuration 14 in contact with adjacent bones; being customizable to a particular anatomy; and providing an open deformable cage configuration capable of optimizing contact of bone graft materials with adjacent bones.

The present invention may include embodiments of a bone fusion system. As shown in FIGS. 1-4, in such an embodiment, the bone fusion system may include the bone fusion device 10 comprising deformable segments 11, and a bone fusion device delivery and deployment system comprising the internal rod 30 and the pushing tube 31.

Some embodiments of the bone fusion device 10 can be delivered to a target bone site, for example, the intervertebral space 12, in the compressed, or unexpanded, configuration 13. As a result, the bone fusion device 10 may be delivered to the intervertebral space 12 utilizing a minimally invasive surgical procedure. Once in a desired position within the intervertebral space 12, the deformable segments 11 can be expanded to the deployed configuration 14 in contact with the adjacent vertebral bodies 17. In certain embodiments, the deformable segments 11 may be expanded with a mechanical force. In certain embodiments, the deformable segments 11 may be deformed in varying degrees and configurations, thereby allowing for control of the deployed size and shape of the bone fusion implant 10.

As shown in the embodiment in FIG. 1, the bone fusion device 10 can include the implantable elongated structure 15 of segments comprising at least two anchor portions 16 and one or more deformable segments 11. The elongated structure 15 can have various geometric configurations, such as tubular, oval, or rectangular, for example. Some embodiments of a system can include the proximal anchor portion 20 and the distal anchor portion 21. A deformable segment 11 can be attached to one or both of the proximal anchor portion 20 and the distal anchor portion 21. In embodiments having more than one deformable segment 11, the deformable segments 11 can alternate with anchor portions 16. The alternating deformable segments 11 can be spaced at particular intervals along the longitudinal axis 26 of the device 10.

In some embodiments, the deformable segments 11 can comprise deformable members 27 lying parallel to the longitudinal axis 26 of the device 10. In some embodiments, the deformable members 27 can be spaced about the periphery, for example, the circumference, of the device 10 with equal spacing, or with varying sized spaces, between the deformable members 27, depending on the desired deployed configuration 14 of the deformable segment 11. Embodiments of the bone fusion device 10 can comprise various biocompatible materials, for example, titanium and/or stainless steel, that are capable of being deformed into the expanded configuration 14 and maintaining that configuration 14 for the duration of the functional life of the device 10. In certain embodiments, the anchor portions 16 can have the hollow lumen 28 so that bone growth promoting materials can be placed inside the anchor portions 16 and through the anchor portions 16 into and through the deformable segments 11.

The deformable segments 11 can each have the same or varying characteristics and dimensions. For example, the deformable segments 11 can comprise deformable members 27, for example, deformable wires 27, having the same or different material(s), gauge, shape, length, and number of wires 27. Varying the characteristics can allow a particular deformable segment 11 to deform more or less easily, to a greater or lesser degree, and/or more or less in one direction than in another segment 11. As a result, the ultimate diameter or configuration of each of the deformable segments 11 and of the overall device 10 in its expanded state 14 can vary. This can allow the bone fusion device 10 to be customized for a particular joint, such as the intervertebral 12 joint.

In some embodiments of a system, longitudinal compression of the proximal anchor portion 20 toward the distal anchor portion 21 of the bone fusion device 10 can provide uniform expansion of the deformable members 11 along the longitudinal axis 26 of the device 10. In other embodiments, expansion of the deformable members 11 may not be uniform so as to provide customizable deployed configurations of the device 10 adapted to interface with and support particular anatomical configurations. For example, as shown in FIG. 2, the deformable members 27 in the middle deformable segment 11 can be longer than the deformable members 27 in the deformable segments 11 adjacent the proximal and distal anchor portions 20, 21, respectively, such that the deformable members 27 in the middle deformable segment 11 can deform to a larger dimension than the deformable members 27 in the other deformable segments 11. Some embodiments of the bone fusion system can include the bone fusion device 10 having one end of the device 10 adapted to expand to a greater degree than the opposite end to help maintain and/or restore the natural anatomy of a fused spinal 40 segment.

In certain embodiments, the deformable members 27 can be pre-stressed so that when deformed from their unexpanded configuration 13, the deformable members 27 will bend into particular directions so as to provide support along a particular transverse axis (such as vertical and not horizontal). In some embodiments, the deformable members 27 can have strength sufficient to maintain the device 10 in its expanded geometry 14 when exposed to compressive forces translated through the adjacent vertebral bodies 17. In some embodiments, the deformable segments 11 can include features, such as a particular contour or surface projections, that promote anchoring of the expanded deformable segments 11 into adjacent vertebral body endplates 43.

Some embodiments of the bone infusion system can include the bone fusion device delivery and deployment system comprising the internal rod 30 and the pushing tube 31, as shown in FIGS. 3 and 4. The internal rod 30 can be detachably attached to the distal anchor portion 21, and the pushing tube 31 can be detachably attached to the proximal anchor portion 20, using various attachment mechanisms. For example, in some embodiments, the internal rod 30 may be attached to the distal anchor portion 21 with mating threads (not shown), and the pushing tube 31 may be attached to the proximal anchor portion 20 with mating threads (not shown). In certain embodiments, both the internal rod 30 and the pushing tube 31 can be detachably attached to the bone fusion device 10 using identically sized threads as to allow for detachment of the internal rod 30 and the pushing tube 31 from the bone fusion device implant 10 by simultaneously rotating both the internal rod 30 and the pushing tube 31.

In some embodiments, the internal rod 30 and the pushing tube 31 can operate together to cause the deformable members 27 to deform outwardly. The internal rod 30 and the distal end 25 of the bone fusion device 10 attached to the rod 30 can be held in a fixed position in the intervertebral space 12. The pushing tube 31 can be translated forward so as to push the proximal end 24 of the bone fusion device 10 attached thereto toward the fixed position, distal end 25 of the device 10. As the pushing tube 31 is translated forward, the linear compressive force of such translation/pushing along the longitudinal axis 26 of the device 10 can cause the deformable members 27 to deform outwardly to the expanded, deployed configuration 14. In this configuration 14, all of the deformable members 11 can be bent at predetermined angles, depending on factors, including, for example, the arrangement of the deformable segments 11 relative to the anchor portions 16, and the gauge, shape, length, and number of deformable members 27. The bent deformable members 27 can serve to contact the adjacent vertebral body endplates 43 to restore the normal height, or a desired height, of the intervertebral disc 44 and to prevent movement of the implanted device 10 during its functional life.

Some embodiments of the bone fusion system can further comprise a handle (not shown) positioned outside the patient's body, as described herein. The proximal end 24 of the internal rod 30 can interface with the handle so that the rod 30 and the distal end 25 of the bone fusion device 10 attached to the rod 30 can be held stationary. The pushing tube 31 can operatively interface with the handle so that the pushing rod 31 and the proximal end 24 of the bone fusion device 10 can be translated forward toward the stationary distal end 25 of the bone fusion device 10. The handle and the pushing tube interface can include a mechanism by which excessive translation of the pushing tube 31 and the proximal end 24 of the bone fusion device 10 can be avoided. For example, the excessive translation prevention mechanism may include in or on the handle indicia of the degree of deformable member expansion, or other mechanical translation-limiting components.

Some embodiments of the bone fusion system can further include bone growth promoting materials. Such bone growth promoting materials can be loaded or inserted into the interior of the bone fusion device 10 to facilitate or promote bone growth with and between the adjacent bones, such as vertebral bodies 17. Bone growth promoting materials can comprise, for example, a bone graft material, a bone morphogenic protein (BMP), a demineralized bone matrix (DBM), mesenchymal stem cells, a LIM mineralization protein (LMP), and/or any other suitable bone growth promoting material or substance. The bone growth promoting materials can be loaded into the bone fusion device 10 prior to or after implantation of the device 10. In some embodiments of such a system, the open structure of the expanded deformable member cage can minimize restriction of movement of the bone growth promoting materials and thus facilitate contact of the bone growth promoting materials in the device 10 with adjacent vertebral bodies 17 (or other bones).

Some embodiments of the bone fusion system can further include a plurality of the bone fusion devices 10, each capable of various deployed sizes and/or configurations. Such design variability can provide a surgeon with options for implanting the bone fusion device(s) 10 suited for particular patients. In certain embodiments of the system, one of the bone fusion devices 10 may be delivered into a first portion of the target intervertebral space 12 and another one of the bone fusion devices 10 may be delivered into a second portion of the target intervertebral space 12.

Some embodiments of the bone fusion system can further include other surgical instruments, for example, for removing an intervertebral disc, preparing the vertebral bodies 17 for receipt of the bone fusion device 10, and/or distracting the vertebral bodies 17 for implantation of the bone fusion device 10.

The present invention may include embodiments of a bone fusion device kit. As shown in FIGS. 1-4, in such an embodiment, the bone fusion device kit may include the bone fusion device 10 comprising deformable segments 11, and a bone fusion device delivery and deployment system comprising the internal rod 30 and the pushing tube 31.

Some embodiments of the bone fusion device 10 can be delivered to a target bone site, for example, the intervertebral space 12, in the unexpanded configuration 13. As a result, the bone fusion device 10 may be delivered to the intervertebral space 12 utilizing a minimally invasive surgical procedure. Once in a desired position within the intervertebral space 12, the deformable segments 11 can be expanded to the deployed configuration 14 in contact with the adjacent vertebral bodies 17. In certain embodiments, the deformable segments 11 may be expanded with a mechanical force. In certain embodiments, the deformable segments 11 may be deformed in varying degrees and configurations, thereby allowing for control of the deployed size and shape of the bone fusion implant 10.

As shown in the embodiment in FIG. 1, the bone fusion device 10 can include an implantable elongated structure 15 of segments comprising at least two anchor portions 16 and one or more deformable segments 11. The elongated structure 15 can have various geometric configurations, such as tubular, oval, or rectangular, for example. Some embodiments can include the proximal anchor portion 20 and the distal anchor portion 21. A deformable segment 11 can be attached to one or both of the proximal anchor portion 20 and the distal anchor portion 21. In embodiments having more than one deformable segment 11, the deformable segments 11 can alternate with the anchor portions 16. The alternating deformable segments 11 can be spaced at particular intervals along the longitudinal axis 26 of the device 10.

In some embodiments, the deformable segments 11 can comprise deformable members 27 lying parallel to the longitudinal axis 26 of the device 10. In some embodiments, the deformable members 27 can be spaced about the circumference, or periphery, of the device 10 with equal spacing, or with varying sized spaces, between the deformable members 27, depending on the desired deployed configuration of the deformable segment 11. Embodiments of the bone fusion device 10 can comprise various biocompatible materials, for example, titanium and/or stainless steel, that are capable of being deformed into the expanded configuration 14 and maintaining that configuration 14 for the duration of the functional life of the device 10. In certain embodiments, the anchor portions 16 can have the hollow lumen 28 so that bone growth promoting materials can be placed inside the anchor portions 16 and through the anchor portions 16 into and through the deformable segments 11.

The deformable segments 11 can each have the same or varying characteristics and dimensions. For example, the deformable segments 11 can comprise the same or different material(s), gauge, shape, length, and number of deformable members, or wires 27. Varying the characteristics can allow a particular deformable segment 11 to deform more or less easily, to a greater or lesser degree, and/or more or less in one direction than in another segment 11. As a result, the ultimate diameter or configuration of each of the deformable segments 11 and of the overall device 10 in its expanded state 14 can vary. This can allow the bone fusion device 10 to be customized for a particular joint, such as the intervertebral 12 joint.

In some embodiments of a kit, longitudinal compression of the proximal anchor portion 20 toward the distal anchor portion 21 of the bone fusion device 10 can provide uniform expansion of the deformable members 27 along the longitudinal axis 26 of the device 10. In other embodiments, expansion of the deformable members 27 may not be uniform so as to provide customizable deployed configurations of the device 10 adapted to interface with and support particular anatomical configurations. For example, as shown in FIG. 2, the deformable members 27 in the middle deformable segment 11 can be longer than the deformable members 27 in the deformable segments 11 adjacent the proximal and distal anchor portions, 20, 21, respectively, such that the deformable members 27 in the middle deformable segment 11 can deform to a larger dimension than the deformable members 27 in the other deformable segments 11. Some embodiments of the bone fusion device kit can include the bone fusion device 10 having one end of the device 10 adapted to expand to a greater degree than the opposite end to help maintain and/or restore the natural anatomy of a fused spinal 40 segment.

In certain embodiments, the deformable members 27 can be pre-stressed so that when deformed from their unexpanded configuration 13, the deformable members 27 will bend into particular directions so as to provide support along a particular transverse axis (such as vertical and not horizontal). In some embodiments, the deformable members 27 can have strength sufficient to maintain the device 10 in its expanded geometry 14 when exposed to compressive forces translated through the adjacent vertebral bodies 17. In some embodiments, the deformable segments 11 can include features, such as a particular contour or surface projections, that promote anchoring of the expanded deformable segments 11 into adjacent vertebral body endplates 43.

Some embodiments of the bone infusion device kit can include the bone fusion device delivery and deployment system comprising the internal rod 30 and the pushing tube 31, as shown in FIGS. 3 and 4. The internal rod 30 can be detachably attached to the distal anchor portion 21, and the pushing tube 31 can be detachably attached to the proximal anchor portion 20, using various attachment mechanisms. For example, in some embodiments, the internal rod 30 may be attached to the distal anchor portion 21 with mating threads (not shown), and the pushing tube 31 may be attached to the proximal anchor portion 20 with mating threads (not shown). In certain embodiments, both the internal rod 30 and the pushing tube 31 can be detachably attached to the bone fusion device 10 using identically sized threads as to allow for detachment of the internal rod 30 and the pushing tube 31 from the bone fusion device implant 10 by simultaneously rotating both the internal rod 30 and the pushing tube 31.

In some embodiments, the internal rod 30 and the pushing tube 31 can operate together to cause the deformable members 27 to deform outwardly. The internal rod 30 and the distal end 25 of the bone fusion device 10 attached to the rod 30 can be held in a fixed position in the intervertebral space 12. The pushing tube 31 can be translated forward so as to push the proximal end 24 of the bone fusion device 10 attached thereto toward the fixed position, distal end 25 of the device 10. As the pushing tube 31 is translated forward, the linear compressive force of such translation/pushing along the longitudinal axis 26 of the device 10 can cause the deformable members 27 to deform outwardly to the expanded, deployed configuration 14. In this configuration 14, all of the deformable members 27 can be bent at predetermined angles, depending on factors, including, for example, the arrangement of the deformable segments 11 relative to the anchor portions 16, and the gauge, shape, length, and number of deformable members 27. The bent deformable members 27 can serve to contact the adjacent vertebral body endplates 43 to restore the normal height, or a desired height, of the intervertebral disc 44 and to prevent movement of the implanted device 10 during its functional life.

Some embodiments of the bone fusion device kit can further comprise a handle (not shown) positioned outside the patient's body, as described herein. The proximal end 24 of the internal rod 30 can interface with the handle so that the rod 30 and the distal end 25 of the bone fusion device 10 attached to the rod 30 can be held stationary. The pushing tube 31 can operatively interface with the handle so that the pushing rod 31 and the proximal end 24 of the bone fusion device 10 can be translated forward toward the stationary distal end 25 of the bone fusion device 10. The handle and the pushing tube interface can include a mechanism by which excessive translation of the pushing tube 31 and the proximal end 24 of the bone fusion device 10 can be avoided. For example, the excessive translation prevention mechanism may include in or on the handle indicia of the degree of deformable member expansion, or other mechanical translation-limiting components.

Some embodiments of the bone fusion device kit can further include bone growth promoting materials. Such bone growth promoting materials can be loaded or inserted into the interior of the bone fusion device 10 to facilitate or promote bone growth with and between the adjacent bones, such as vertebral bodies 17. Bone growth promoting materials can comprise, for example, a bone graft material, a bone morphogenic protein (BMP), a demineralized bone matrix (DBM), mesenchymal stem cells, a LIM mineralization protein (LMP), and/or any other suitable bone growth promoting material or substance. The bone growth promoting materials can be loaded into the bone fusion device 10 prior to or after implantation of the device 10. In some embodiments of such a kit, the open structure of the expanded deformable member cage can minimize restriction of movement of the bone growth promoting materials and thus facilitate contact of the bone growth promoting materials in the device 10 with adjacent vertebral bodies 17 (or other bones).

Some embodiments of the bone fusion device kit can further include a plurality of the bone fusion devices 10, each capable of various deployed sizes and/or configurations. Such design variability can provide a surgeon with options for implanting the bone fusion device(s) 10 suited for particular patients or anatomy being treated. In certain embodiments of the kit, one of the bone fusion devices 10 may be delivered into a first portion of the target intervertebral space 12 and another one of the bone fusion devices 10 may be delivered into a second portion of the target intervertebral space 12.

Some embodiments of the bone fusion device kit can further include other surgical instruments, for example, for removing the intervertebral disc 44, preparing the vertebral bodies 17 for receipt of the bone fusion device 10, and/or distracting the vertebral bodies 17 for implantation of the bone fusion device 10.

The present invention may include embodiments of a method for fusing bone. Such a method can comprise utilizing the bone fusion device 10, system, and/or kit as described herein. For example, one such method can include providing the bone fusion device 10 comprising one or more deformable segments 11, as shown in FIGS. 1-4.

Some embodiments of the method can further include delivering the bone fusion device 10 to a target bone site, for example, the intervertebral space 12, in the compressed, or unexpanded, configuration 13. Accordingly, the unexpanded bone fusion device 10 can be delivered into the intervertebral space 12 utilizing a minimally invasive surgical procedure. Once the bone fusion device 10 is in a desired position within the intervertebral space 12, some embodiments of the method can further include expanding the deformable segment(s) 11 into the deployed configuration 14 in contact with the adjacent vertebral bodies 17. In certain embodiments, the deformable segment(s) 11 may be expanded with a mechanical force. In certain embodiments, the deformable segment(s) 11 may be expanded, or deformed, in varying degrees and configurations, which may allow for better control of the size and shape of the bone fusion implant 10 as compared to conventional bone fusion cages.

As shown in the embodiment in FIG. 1, the bone fusion device 10 can include the implantable elongated structure 15 of segments comprising at least two anchor portions 16 and one or more deformable segments 11. The deformable segment 11 can be attached to one or both of the proximal anchor portion 20 and the distal anchor portion 21 of the bone fusion device 10. In embodiments having more than one deformable segment 11, the deformable segments 11 can alternate with the anchor portions 16. The alternating deformable segments 11 can be spaced at particular intervals along the longitudinal axis 26 of the device 10. In some embodiments, the deformable segments 11 can comprise deformable members 27 lying parallel to the longitudinal axis 26 of the device 10. The deformable members 27 can be spaced about the periphery, or circumference, of the device 10 with equal spacing, or with varying sized spaces, between the deformable members 27, depending on the desired deployed configuration of the deformable segment 11.

Some embodiments of such a method can further include selecting the characteristics and dimensions of the deformable segments 11. For example, the deformable segments 11 can comprise deformable members 27, for example, wires 27, having the same or different material(s), gauge, shape, length, and number of deformable members 27. Varying the characteristics can allow a particular deformable segment 11 to deform more or less easily, to a greater or lesser degree, and/or more or less in one direction than in another segment 11. As a result, the ultimate diameter or configuration of each of the deformable segments 11 and of the overall device 10 in its expanded state 14 can vary. This can allow the bone fusion device 10 to be customized for a particular joint, such as the intervertebral 12 joint.

Some embodiments of such a method can further include expanding the deformable segments 11 in a uniform manner along the longitudinal axis 26 of the device 10. Alternatively, embodiments of such a method can further include expanding the deformable members 27 in a non-uniform manner and in particular directions so as to provide support, for example, along a particular transverse axis/axes (such as vertical and not horizontal). In this way, the deformable segments 11 can be expanded so as to provide customizable deployed configurations of the device 10 adapted to interface with and support particular anatomical configurations. For example, as shown in FIG. 2, the deformable members 27 in the middle deformable segment 11 can be longer than the deformable members 27 in the deformable segments 11 adjacent the proximal and distal anchor portions, 20, 21, respectively, such that the deformable members 27 in the middle deformable segment 11 can deform to a larger dimension than the deformable members 27 in the other deformable segments 11. Some embodiments of the bone fusion device 10 can have one end of the device 10 adapted to expand to a greater degree than the opposite end. As a result, some embodiments of a method may further include exerting a greater force at one aspect, for example, the anterior 45 or posterior 42 aspect, of adjacent vertebral bodies 17 so as to maintain and/or restore the natural anatomy, or a desired intervertebral space height, in a fused spinal 40 segment.

Some embodiments of such a method can further include promoting anchoring of the expanded deformable segments 11 into adjacent vertebral body endplates 43 by providing the deformable segments 11 with features such as a particular contour or surface projections for that purpose.

Some embodiments of such a method can further include deforming the deformable members 11 into the expanded configuration 14 capable of maintaining that configuration 14 for the duration of the functional life of the device 10.

Some embodiments of such a method can further include placing bone growth promoting materials inside the hollow lumen 28 of the anchor portions 16 to allow movement of the materials in and through the expanded deformable member cage, thereby facilitating or promoting bone growth with and between the adjacent bones, such as vertebral bodies 17.

Some embodiments of such a method can further include detachably attaching the inner rod 30 to the distal anchor portion 21 of the bone fusion device 10, and detachably attaching the pushing tube 31 to the proximal anchor portion 21, as shown in FIGS. 3 and 4. The inner rod 30 and pushing tube 31 may be detachably attached to the bone fusion device distal and proximal anchor portions, 21, 20, respectively, using various attachment mechanisms, for example, with mating threads (not shown). If attachments are made with threads, once the bone fusion device 10 is deployed, the inner rod 30 and pushing tube 31 can be detached from the bone fusion device 10 by unthreading. In embodiments in which identically sized threads are used, both the internal rod 30 and the pushing tube 31 can be detached from the bone fusion device implant 10 by simultaneously rotating both the internal rod 30 and the pushing tube 31.

In some embodiments, the internal rod 30 and the pushing tube 31 can be operated together to cause the deformable members 11 to deform outwardly. The internal rod 30 and the distal end 25 of the bone fusion device 10 attached to the rod 30 can be held in a fixed position in the intervertebral space 12. The pushing tube 31 can be translated forward so as to push the proximal end 24 of the bone fusion device 10 attached thereto toward the fixed position, distal end 25 of the device 10. As the pushing tube 31 is translated forward, the linear compressive force of such translation/pushing along the longitudinal axis 26 of the device 10 can cause the deformable members 11 to deform outwardly to the expanded, deployed configuration 14. The expanded deformable members 27 can serve to contact the adjacent vertebral body endplates 43 to restore the normal height, or a desired height, of the intervertebral disc 44 and to prevent movement of the implanted device 10 during its functional life.

In some embodiments of a method, the proximal end 24 of the internal rod 30 and pushing tube 31 can interface with a handle (not shown) so that the rod 30 and the distal end 25 of the bone fusion device 10 attached to the rod 30 can be held stationary and so that the pushing tube 31 and the proximal end 24 of the bone fusion device 10 can be translated forward toward the stationary distal end 25 of the bone fusion device 10. Some embodiments of such a method can further include avoiding or preventing excessive translation of the pushing tube 31 and the proximal end 24 of the bone fusion device 10.

Some embodiments of such a method can further include providing a plurality of the bone fusion devices 10, each capable of various deployed sizes and/or configurations. Such design variability can provide a surgeon with options for implanting the bone fusion device(s) 10 suited for particular patients.

In some embodiments of a method, one of the bone fusion devices 10 may be delivered into a first portion, or side, of the target intervertebral space 12 and another one of the bone fusion devices 10 may be delivered into a second portion, or side, of the target intervertebral space 12. In certain embodiments of such methods, the first and second bone fusion devices 10 can be positioned in the intervertebral space 12 in adjacent side-by-side relation. As an example, a first side of the intervertebral space 12 can be accessed and a first unexpanded bone fusion device 10 can be delivered into the first side of the space 12 and expanded into the deployed configuration 14. Once the first bone fusion device 10 is deployed and implanted, a second side of the intervertebral space 12 can be accessed. A second unexpanded bone fusion device 10 can be delivered into the second side of the space 12 and expanded into the deployed configuration 14. Alternatively, the first side of the intervertebral space 12 can be accessed, and then the second side of the intervertebral space 12 can be accessed. Next, either the first or the second bone fusion device 10 can be delivered into its respective side of the intervertebral space 10 and expanded into the deployed configuration 14, followed by delivery and expansion of the other bone fusion device 10 into the deployed configuration 10. The order and/or degree of expansion of each of the bone fusion devices 10 can be varied, depending on the pathology of the intervertebral space 12 and adjacent vertebral bodies 17, as well as other patient-related and/or surgical technique factors. For example, the first bone fusion device 10 may be partially expanded, followed by partial expansion of the second bone fusion device 10, followed by full expansion of the first device 10, and finally full expansion of the second device 10.

Some embodiments of such a method can further include removing the intervertebral disc 44, preparing the vertebral bodies 17 for receipt of the bone fusion device 10, and/or distracting the vertebral bodies 17 for implantation of the bone fusion device 10.

Embodiments of a bone fusion device 10, system, kit, and method of the present invention can be utilized for facilitating stabilization or fusion of bones. Some embodiments can be advantageously used in the stabilization and fusion of a joint, particularly an intervertebral 12 joint. Embodiments have been described herein with reference to stabilization and fusion of adjacent vertebrae 17. Some embodiments may be applicable for use with various types of joints (for example, intervertebral, ankle, interdigital, etc.) and in various anatomical regions (for example, spine, arms, legs, etc.) of a human or animal body. In the spinal column 40, the devices and methods disclosed may be used at all intervertebral 12 joints, including those in the cervical, thoracic, and lumbar region.

Although the present invention has been described with reference to particular embodiments, it should be recognized that these embodiments are merely illustrative of the principles of the present invention. Those of ordinary skill in the art will appreciate that a spinal fusion device 10, system, kit, and methods of the present invention may be constructed and implemented in other ways and embodiments. For example, an embodiment of the bone fusion device 10 according to the present invention can be delivered to a target bone site using a minimally invasive surgical procedure or an open surgical procedure. Accordingly, the description herein should not be read as limiting the present invention, as other embodiments also fall within the scope of the present invention.

What is claimed is:

1. A bone fusion device, comprising:
   at least two anchor members spaced apart along a longitudinal axis; and
   a plurality of deformable members extending axially between an adjacent pair of said anchor members, said deformable members each individually defining a rounded outer periphery extending axially along said longitudinal axis, said deformable members having an initial configuration that provides the bone fusion device with an unexpanded height in a direction transverse to said longitudinal axis, said initial configuration transitionable to a deformed configuration that provides the bone fusion device with an expanded height in a direction transverse to said longitudinal axis, said expanded height being greater than said unexpanded height; and
   wherein compression of said deformable members along said longitudinal axis outwardly deforms said deformable members from said initial configuration to said deformed configuration to transition the bone fusion device from said unexpanded height to said expanded height and into contact with two adjacent bone structures,
   wherein said rounded outer periphery of said deformable members comprises a circular outer cross section,
   wherein said circular cross section of at least one of said deformable members has a first outer diameter; and
   wherein said circular cross section of at least one other of said deformable members has a second outer diameter different from said first outer diameter.

2. The bone fusion device of claim 1, wherein said circular outer cross section of said deformable members is in the shape of a circle having a constant outer diameter along said longitudinal axis.

3. The bone fusion device of claim 1, wherein said anchor members comprise tubular shaped discs; and wherein said deformable members are attached to oppositely facing end surfaces of said tubular shaped discs.

4. The bone fusion device of claim 3, wherein said deformable members are welded to said oppositely facing end surfaces of said tubular shaped discs.

5. The bone fusion device of claim 1, wherein said deformable members and said anchor members cooperate to provide an elongated structure extending along said longitudinal axis and having a cylindrical-shaped tubular configuration when in said initial configuration.

6. The bone fusion device of claim 5, wherein said cylindrical-shaped tubular configuration has a circular outer cross section extending along said longitudinal axis.

7. The bone fusion device of claim 5, wherein said cylindrical-shaped tubular configuration defines a hollow interior extending along said longitudinal axis between said plurality of deformable members; and further comprising a bone growth promoting material positioned within said hollow interior.

8. The bone fusion device of claim 1, wherein said deformable members are each arranged generally parallel with said longitudinal axis and generally parallel with one another when in said initial configuration.

9. The bone fusion device of claim 1, further comprising at least three of said anchor members spaced apart from one another along said longitudinal axis; wherein a first set of said plurality of deformable members extends axially between a first of said anchor members and a second of said anchor members to define a first deformable segment of the bone fusion device; and wherein a second set of said plurality of deformable members extends axially between said second anchor member and a third of said anchor members to define a second deformable segment of the bone fusion device.

10. The bone fusion device of claim 1, further comprising: an internal rod extending along said longitudinal axis and detachably engaged to a distal one of said anchor members; and a pushing tube slidably engaged about said internal rod and detachably engaged to a proximal one of said anchor members; and wherein translation of said pushing tube and said proximal anchor member along said longitudinal axis relative to said inner rod toward said distal anchor member compresses said deformable members so as to deform said deformable members to said deformed configuration.

11. The bone fusion device of claim 10, wherein said internal rod and said distal anchor member are threadedly engaged to one another by a first set of mating threads; and wherein said pushing tube and said proximal anchor member are threadedly engaged to one another by a second set of mating threads.

12. The bone fusion device of claim 11, wherein said first set of mating threads is configured identical to said second set of mating threads such that said internal rod and said pushing tube are detachable from said distal and proximal anchor members by simultaneous rotation of said internal rod and said pushing tube.

13. A bone fusion device, comprising:
at least two anchor members spaced apart along a longitudinal axis; and
a plurality of wire members extending axially between an adjacent pair of said anchor members, said wire members having an initial configuration that provides the bone fusion device with an unexpanded height in a direction transverse to said longitudinal axis, said initial configuration transitionable to a deformed configuration that provides the bone fusion device with an expanded height in a direction transverse to said longitudinal axis, said expanded height being greater than said unexpanded height;
an internal rod extending along said longitudinal axis and detachably engaged to a distal one of said anchor members;
a pushing tube slidably engaged about said internal rod and detachably engaged to a proximal one of said anchor members;
wherein translation of said pushing tube and said proximal anchor member along said longitudinal axis relative to said inner rod toward said distal anchor member compresses said wire members so as to deform said wire members to said deformed configuration,
wherein said internal rod and said distal anchor member are threadedly engaged to one another by a first set of mating threads,
wherein said pushing tube and said proximal anchor member are threadedly engaged to one another by a second set of mating threads,
wherein said first set of mating threads is configured identical to said second set of mating threads such that said internal rod and said pushing tube are detachable from said distal and proximal anchor members by simultaneous rotation of said internal rod and said pushing tube, and
wherein compression of said wire members along said longitudinal axis outwardly deforms said wire members from said initial configuration to said deformed configuration to transition the bone fusion device from said unexpanded height to said expanded height and into contact with two adjacent bone structures.

14. The bone fusion device of claim 13, wherein said wire members each individually define a circular outer cross section extending axially along said longitudinal axis.

15. The bone fusion device of claim 14, wherein said circular outer cross section of said wire members defines a substantially uniform outer diameter along said longitudinal axis.

16. The bone fusion device of claim 13, wherein each of said wire members has a substantially uniform wire gauge.

17. The bone fusion device of claim 13, wherein at least one of said wire members has a first wire gauge; and wherein at least one other of said wire members has a second wire gauge different from said first wire gauge.

18. The bone fusion device of claim 13, wherein said wire members and said anchor members cooperate to provide an elongated structure extending along said longitudinal axis and having a cylindrical-shaped tubular configuration when in said initial configuration.

19. The bone fusion device of claim 18, wherein said cylindrical-shaped tubular configuration has a circular outer cross section extending along said longitudinal axis.

20. The bone fusion device of claim 13, wherein said wire members are each arranged generally parallel with said longitudinal axis and generally parallel with one another when in said initial configuration.

21. The bone fusion device of claim 13, further comprising at least three of said anchor members spaced apart from one another along said longitudinal axis; wherein a first set of said plurality of wire members extends axially between a first of said anchor members and a second of said anchor members to define a first deformable segment of the bone fusion device; and wherein a second set of said plurality of wire members extends axially between said second anchor member and a third of said anchor members to define a second deformable segment of the bone fusion device.

22. The bone fusion device of claim 13, further comprising:
an internal rod extending along said longitudinal axis and detachably engaged to a distal one of said anchor members; and
a pushing tube slidably engaged about said internal rod and detachably engaged to a proximal one of said anchor members; and
wherein translation of said pushing tube and said proximal anchor member along said longitudinal axis relative to said inner rod toward said distal anchor member compresses said wire members so as to deform said wire members to said deformed configuration.

23. The bone fusion device of claim 22, wherein said internal rod and said distal anchor member are threadedly engaged to one another by a first set of mating threads; wherein said pushing tube and said proximal anchor member are threadedly engaged to one another by a second set of mating threads; and wherein said first set of mating threads is configured identical to said second set of mating threads such that said internal rod and said pushing tube are detachable from said distal and proximal anchor members by simultaneous rotation of said internal rod and said pushing tube.

24. A bone fusion device, comprising:
at least two anchor members spaced apart along a longitudinal axis;
a plurality of wire members extending axially between an adjacent pair of said anchor members, said wire members each individually defining, a rounded outer periphery extending axially along said longitudinal axis, said wire members having an initial configuration that provides the bone fusion device with an unexpanded height in a direction transverse to said longitudinal axis, said initial configuration transitionable to a deformed configuration that provides the bone fusion device with an expanded height in a direction transverse to said longitudinal axis, said expanded height being greater than said unexpanded height;

wherein compression of said wire members along said longitudinal axis outwardly deforms said wire members from said initial configuration to said deformed configuration to transition the bone fusion device from said unexpanded height to said expanded height and into contact with two adjacent bone structures;

wherein said rounded outer periphery of said wire members comprises a circular outer cross section;

wherein said circular cross section of at least one of said wire members has a first outer diameter; and wherein said circular cross section of at least one other of said wire members has a second outer diameter different from said first outer diameter.

* * * * *